United States Patent
Kiribayashi et al.

(10) Patent No.: US 8,222,229 B2
(45) Date of Patent: Jul. 17, 2012

(54) PERITONEAL DIALYSIS METHOD

(75) Inventors: Kei Kiribayashi, Hiroshima (JP); Noriaki Yorioka, Hiroshima (JP)

(73) Assignee: Kowa Co., Ltd., Nagoya-shi (JP)

( * ) Notice: Subject to any disclaimer, the term of this patent is extended or adjusted under 35 U.S.C. 154(b) by 1384 days.

(21) Appl. No.: 10/533,538

(22) PCT Filed: Nov. 20, 2003

(86) PCT No.: PCT/JP03/14790
§ 371 (c)(1), (2), (4) Date: May 2, 2005

(87) PCT Pub. No.: WO2004/045679
PCT Pub. Date: Jun. 3, 2004

(65) Prior Publication Data
US 2006/0019925 A1 Jan. 26, 2006

Related U.S. Application Data

(60) Provisional application No. 60/427,980, filed on Nov. 21, 2002.

(51) Int. Cl.
*A61K 31/7076* (2006.01)
*A61K 31/7052* (2006.01)
*A61K 31/70* (2006.01)

(52) U.S. Cl. .............. 514/47; 514/46; 514/23; 536/27.6

(58) Field of Classification Search ............. 514/23, 514/47, 46; 536/27.6
See application file for complete search history.

(56) References Cited

U.S. PATENT DOCUMENTS 5,547,942 A 8/1996 Rapaport
5,871,477 A * 2/1999 Isono et al. ............. 604/410

FOREIGN PATENT DOCUMENTS

| JP | 9-143063 | 6/1997 |
| WO | 94/18216 | 8/1994 |
| WO | 95/14478 | 6/1995 |

OTHER PUBLICATIONS

Shukolyukov et al. (Mitokohondrii, Mol. Mekh. Ferment. Reakts., Mater. Vses. Simp. Biokhim. Mitokhondrii, 6th (1972), Meeting Date 1970, 189-93. Editor (s): Severin, S. E. "Nauka": Moscow, USSR) (Abstract Sent).*
Yurzhenko ("Parenteral nutrition in the program of therapy of diffuse peritonitis (Russian)", XP002597104, Elsevier Science Publishers, Amsterdam, NL, 1973, vol. 18, No. 7, pp. 36-38.*
Yurzhenko ("Parenteral nutrition in the program of therapy of diffuse peritonitis (Russian)", XP002597104, Elsevier Science Publishers, Amsterdam, NL, 1973, vol. 18, No. 7, pp. 36-38 (English Translation).*
Bergström et al. (Clin Sci Mol Med. Jan. 1978;54(1):51-60) (Abstract sent).*
Yurzhenko ("Parenteral nutrition in the program of therapy of diffuse peritonitis (Russian)", XP002597104, Elsevier Science Publishers, Amsterdam, NL, 1973, vol. 18, No. 7, pp. 36-38).*
Yurzhenko V P, "Parenteral nutrition in the program of therapy of diffuse peritonitis (Russian)", XP002597104, Elsevier Science Publishers, Amsterdam, NL, 1973, vol. 18, No. 7, pp. 36-38.
Ishibashi Y, et al., "Glucose dialysate induces mitochondrial DNA damage in peritoneal mesothelial cells". XP002597105, Elsevier Science Publishers, Amsterdam, NL, 2002, vol. 22, No. 1, pp. 11-21.
Topley N, et al., "Biocompatability of bicarbonate buffered peritoneal dialysis fluids: influence on mesothelial cell and neutrophil function.", Kidney International , May 1996, vol. 49, No. 5, pp. 1447-1456, XP002597106.

* cited by examiner

*Primary Examiner* — Shaojia Anna Jiang
*Assistant Examiner* — Michael C Henry
(74) *Attorney, Agent, or Firm* — Oblon, Spivak, McClelland, Maier & Neustadtm L.L.P.

(57) ABSTRACT

A peritoneal dialysate containing adenosine triphosphate or a salt thereof, and a peritoneal dialysis method using the dialysate.
The peritoneal dialysate is safe and causes less peritoneal injuries even when employed in peritoneal dialysis over a long period of time.

26 Claims, 3 Drawing Sheets

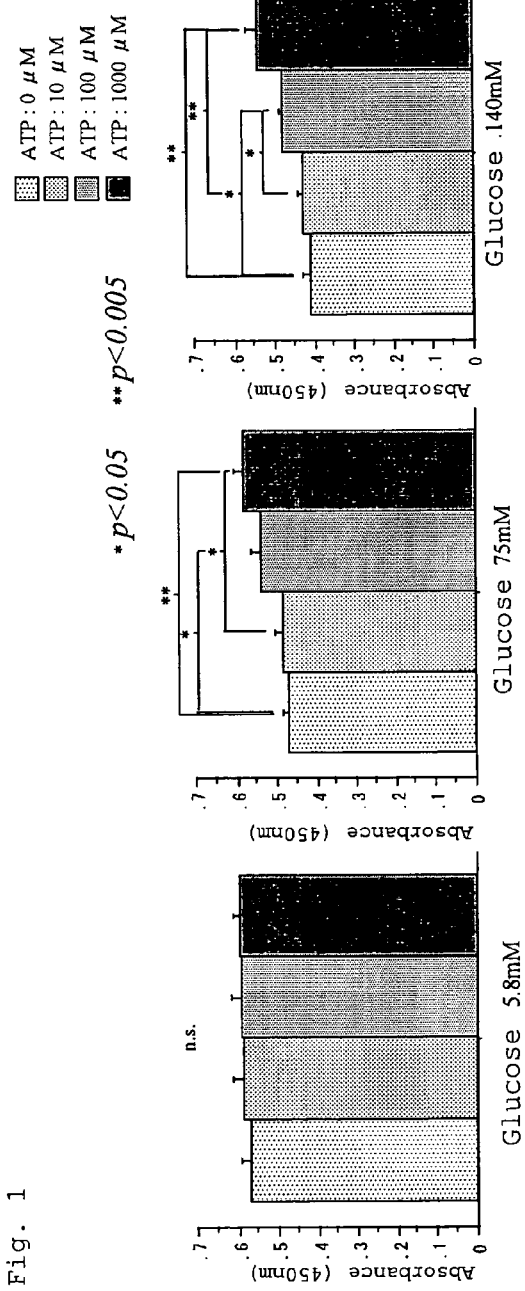
Fig. 1
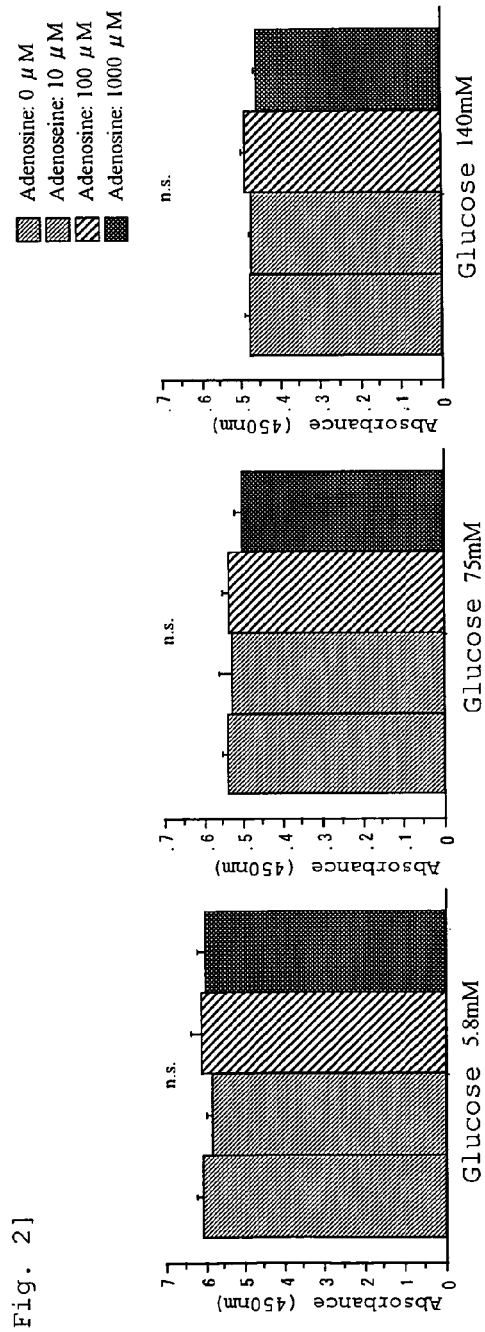
[Fig. 2]

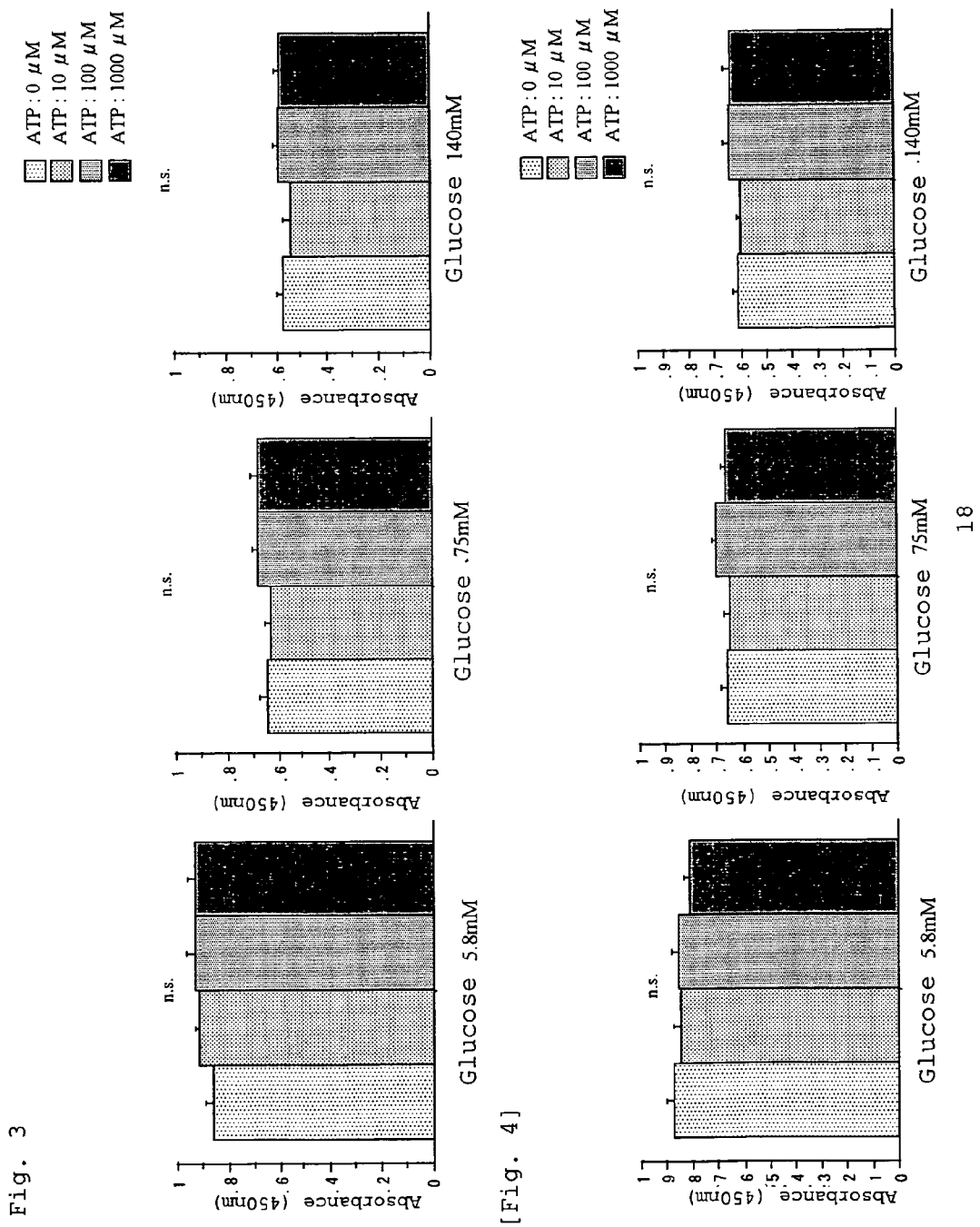

PERITONEAL DIALYSIS METHOD

TECHNICAL FIELD

The present invention relates to a preventive or therapeutic agent for peritoneal injuries which may occur during peritoneal dialysis; to a peritoneal dialysate which is safe and causes less peritoneal injuries or other disorders; and to a peritoneal dialysis method using the peritoneal dialysate.

BACKGROUND ART

In an advanced stage of renal failure, body wastes cannot be removed sufficiently, and therefore, blood levels of uremia-related substances such as urea nitrogen (BUN), creatinine (Cr), phosphorus (P), and potassium (K) increase, to thereby induce a variety of symptoms. The symptoms include increased fatigue, shortness of breath, decreased urine volume, edema, loss of appetite, and in addition to these, hypertension, hyperkalemia, and anemia. If left untreated, patients will eventually die. Therefore, patients suffering from uremia must undergo hemodialysis, peritoneal dialysis, or renal transplantation.

Of these three treatment approaches, peritoneal dialysis has recently come into wide use, for several reasons. Firstly, as compared with hemodialysis, peritoneal dialysis is convenient in that it can be performed at home, requiring neither a special device nor human assistance; peritoneal dialysis is a slow process, and thus can maintain the patient's physical condition stable, without causing low blood pressure or uncomfortable, tired feeling which may otherwise be caused after dialysis; and with peritoneal dialysis, the patient is free from the "lost time" that arises in the case of hemodialysis.

However, when patients are treated with peritoneal dialysis for a long period of time, they may have a problem of possible functional disorder of the peritoneum, involving hardening of the peritoneum, or peritonitis. This disorder is caused by a high dose of glucose employed in peritoneal dialysis, where the peritoneum is used as a semipermeable membrane, and a dialysate containing glucose at a high concentration is introduced into the intraperitoneal cavity through a catheter indwelled therein, and the high-glucose level dialysate is kept in there for 5 to 6 hours before discharge.

DISCLOSURE OF THE INVENTION

To solve the problem above, the present invention provides a peritoneal dialysate which causes less peritoneal injuries and can be employed in peritoneal dialysis continuously over a long period of time, and a peritoneal dialysis method using the dialysate.

The present inventors have focused on peritoneal mesothelial cells lining the peritoneum, and have searched for substances which are capable of preventing peritoneal mesothelial cell injuries caused by high sugar level, and have found that adenosine triphosphate (ATP) or a salt thereof has an effect of preventing peritoneal mesothelial cell injuries, that ATP or a salt thereof thus is useful for a preventive or therapeutic agent for peritoneal injuries, and that a peritoneal dialysate containing ATP or a salt thereof can be employed in peritoneal dialysis for a long period of time, thus completing the present invention.

Accordingly, the present invention provides a peritoneal dialysate containing ATP or a salt thereof.

The present invention also provides a preventive or therapeutic agent for peritoneal injuries, the agent containing ATP or a salt thereof as an active ingredient.

The present invention also provides an agent for treating cell injuries caused by sugar, the agent containing ATP or a salt thereof as an active ingredient.

The present invention also provides use of ATP or a salt thereof in manufacture of a peritoneal dialysate.

The present invention also provides use of ATP or a salt thereof in manufacture of a preventive or therapeutic agent for peritoneal injury.

The present invention also provides use of ATP or a salt thereof in manufacture of an agent for treating cell injuries caused by sugar.

The present invention also provides a peritoneal dialysis method, characterized by comprising using a dialysate containing ATP or a salt thereof in an effective amount.

The present invention also provides a therapeutic method for peritoneal injuries, characterized by administering ATP or a salt thereof in an effective amount.

The present invention also provides a therapeutic method for cell injuries caused by sugar, characterized by administering ATP or a salt thereof in an effective amount.

According to the present invention, there can be obtained a peritoneal dialysate which is safe and which, after use in peritoneal dialysis for a long period of time, causes less peritoneal injuries.

BRIEF DESCRIPTION OF THE DRAWINGS

FIG. 1 shows effect of ATP on decrease in the viability of HPMC (human peritoneal mesothelial cells) attributed to glucose (5.8 mM, 75 mM, and 140 mM) (as measured by absorbance);

FIG. 2 shows effect of adenosine on decrease in the viability of HPMC attributed to glucose (5.8 mM, 75 mM, and 140 mM) (as measured by absorbance);

FIG. 3 shows effect of an ATP receptor antagonist (Suramin, 10 µM) exerted on the ATP's effect on decrease in the viability, as measured by absorbance, of HPMC attributed to glucose (5.8 mM, 75 mM, and 140 mM);

FIG. 4 shows effect of an ATP receptor antagonist (Reactive Blue 2, 30 µM) exerted on the ATP's effect on decrease in the viability, as measured by absorbance, of HPMC attributed to glucose (5.8 mM, 75 mM, and 140 mM)

BEST MODE FOR CARRYING OUT THE INVENTION

Figure 5:
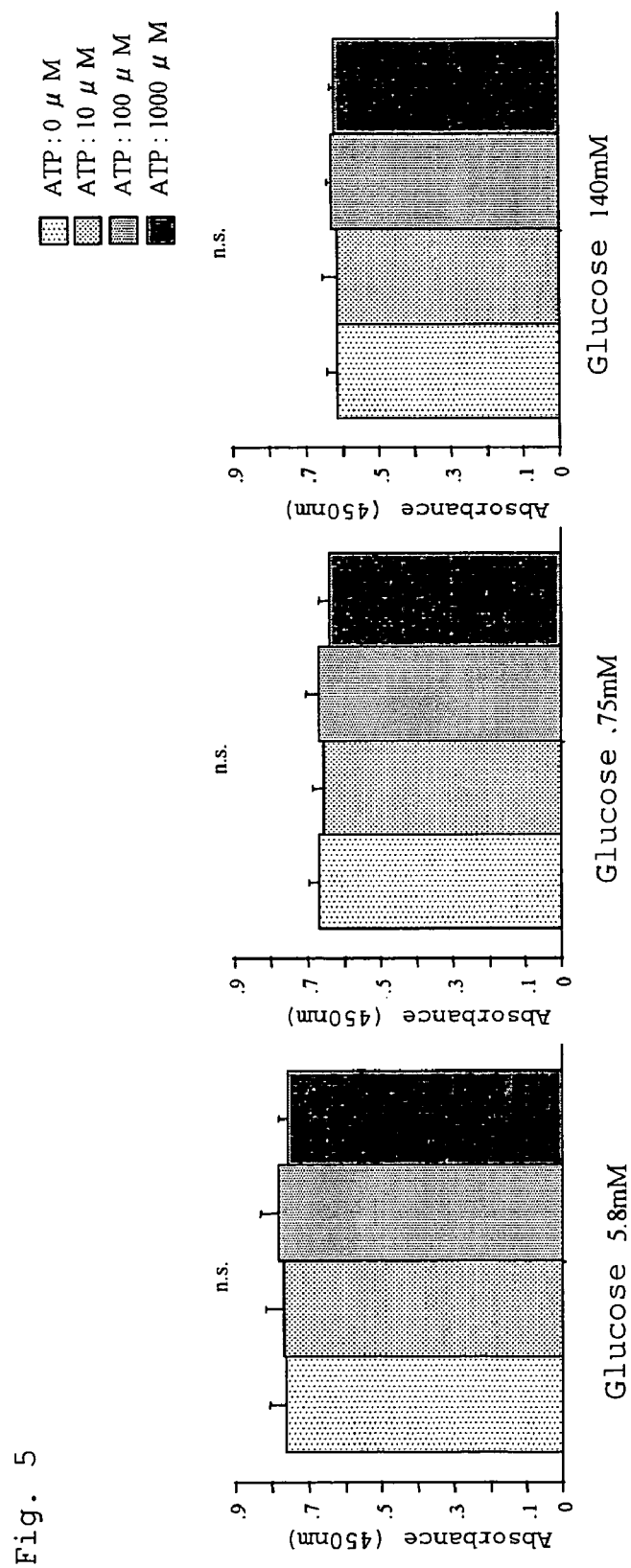
FIG. 5 shows effect of an ATP receptor antagonist (PPADS, 10 µM) exerted on the ATP's effect on decrease in the viability, as measured by absorbance, of HPMC attributed to glucose (5.8 mM, 75 mM, and 140 mM).

Adenosine triphosphate (ATP) employed in the present invention has been known to be an energy source for cells. However, it has remained unknown that ATP can function to prevent injury of cells; in particular, peritoneal mesothelial cells, caused by high sugar level, inter alia, glucose. As shown in the Examples below, peritoneal mesothelial cells which had been pretreated with an ATP receptor antagonist prior to a treatment with ATP did not exhibit any preventive effect for peritoneal mesothelial cell injuries. The results indicate that the therapeutic effect of ATP on cell injuries is not attributed to an action of ATP serving as an energy source after being taken into the cells, but rather to an action of ATP exhibited by the mediation of an ATP receptor.

Preferred examples of the salt of ATP include alkali metal salts such as sodium salts, and alkaline earth metal salts such as magnesium salts and calcium salts.

The peritoneal dialysate of the present invention contains an effective amount of ATP or a salt thereof. The level of the ATP or a salt thereof in the peritoneal dialysate is preferably 10 to 5,000 μM, more preferably 50 to 3,000 μM, even more preferably 50 to 2,000 μM.

The peritoneal dialysate of the present invention desirably contains, in addition to ATP or a salt thereof, glucose and electrolytes. The glucose level is preferably 1,000 to 4,000 mg/dL, more preferably 1,200 to 3,600 mg/dL. As the electrolytes, $Na^+$, $Ca^{2+}$, $Mg^{2+}$, and $Cl^-$ are employed. Preferably, the peritoneal dialysate of the present invention contains $Na^+$ in an amount of 100 to 200 mEq/L, $Ca^{2+}$ in an amount of 4 to 5 mEq/L, $Mg^{2+}$ in an amount of 1 to 2 mEq/L, and $Cl^-$ in an amount of 80 to 120 mEq/L. Preferably, the peritoneal dialysate of the present invention further contains an organic acid such as lactic acid in an amount of 30 to 50 mEq/L. Preferably, the osmotic pressure of the peritoneal dialysate is adjusted to 300 to 700 mOsm/L. The balance is water.

The peritoneal dialysate of the present invention containing ATP or a salt thereof can prevent peritoneal injuries and cell injuries; in particular, peritoneal mesothelial cell injuries, which may otherwise be caused by high sugar level. Examples of the peritoneal injuries include peritonitis, sclerotic encysted peritonitis, intractable prolonged peritonitis, and general peritonitis. However, the preventive or therapeutic agent for peritoneal injury or the therapeutic agent for cell injury according to the present invention may be employed, instead of being in the form of peritoneal dialysate, in drug forms for, for example, peroral administration, intravenous administration, intramuscular administration, and local administration. Drug formulations suitable for these administration routes can be produced by adding one or more pharmacologically acceptable carriers to the agent and then treating the mixture through a routine process known to those skilled in the art.

When an oral solid drug product is prepared, ATP or a salt thereof is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder, or capsules. Additives may be those generally employed in the art. Examples of the excipient include lactate, sucrose, sodium chloride, glucose, starch, calcium carbonate, kaolin, microcrystalline cellulose, and silicic acid; examples of the binder include water, ethanol, propanol, simple syrup, glucose solution, starch solution, liquefied gelatin, carboxymethylcellulose, hydroxypropylcellulose, hydroxypropyl starch, methyl cellulose, ethyl cellulose, shellac, calcium phosphate, and polyvinyl pyrrolidone; examples of the disintegrant include dried starch, sodium arginate, powdered agar, sodium hydrogencarbonate, calcium carbonate, sodium lauryl sulfate, monoglyceryl stearate, and lactose; examples of the lubricant include purified talc, stearic acid salts, borax, and polyethylene glycol; and examples of the sweetening agent include sucrose, orange peel, citric acid, and tartaric acid.

When a liquid drug product for oral administration is prepared, ATP or a salt thereof is mixed with an additive such as a sweetening agent, a buffer, a stabilizer, or a flavoring agent, and the resultant mixture is processed through a routine method, to thereby produce an orally administered liquid drug product such as an internal solution medicine, syrup, or elixir. Examples of the sweetening agent include vanillin; examples of the buffer include sodium citrate; and examples of the stabilizer include tragacanth, acacia, and gelatin.

When an injection product is prepared, ATP or a salt thereof is mixed with an additive such as a pH regulator, a buffer, a stabilizer, an isotonicity agent, or a local anesthetic, and the resultant mixture is processed through a routine method, to thereby produce an injection for subcutaneous injection, intramuscular injection, or intravenous injection. Examples of the pH regulator or buffer include sodium citrate, sodium acetate, and sodium phosphate; examples of the stabilizer include sodium pyrosulfite, EDTA, thioglycollic acid, and thiolactic acid; examples of the local anesthetic include procaine hydrochloride and lidocaine hydrochloride; and examples of the isotonicity agent include sodium chloride and glucose.

The dose of the drug (N.B. not applicable to the case of peritoneal dialysate) of the present invention differs depending on the age, body weight, and conditions of the patient, and the manner and frequency of administration, etc. The daily dose of ATP for an adult is typically 1 to 1,000 mg, and the drug is preferably administered perorally or intravenously once a day or several times a day in a divided manner.

The peritoneal dialysate may be employed in accordance with a conventional peritoneal dialysis method. Specifically, a catheter is introduced into the peritoneal cavity of a patient suffering a renal disease, and a dialysate (typically 1.5 to 2.0 L) containing ATP is intraperitoneally administered to the patient via the catheter. Alternatively, an ATP-containing glucose solution having a physiological glucose level is administered, and, thereafter, a conventional dialysate (such as a solution containing high level glucose) is administered. The thus-infused dialysate or solution is maintained for about five to six hours and then discharged. Typically, the procedure is repeated three to five times a day. The physiological glucose level is 0.08 to 0.16% (w/v).

EXAMPLES

The present invention will next be described in detail by way of examples, which should not be construed as limiting the invention thereto.

Example 1

Peritoneal mesothelial cells (HPMC) were preincubated for three hours in culture media (M199) containing ATP (0, 10, 100, and 1,000 μM). The cells were washed with an HPMC culture medium (saline buffer) and then incubated for eight hours in culture media (M199) containing glucose at three different levels (5.8 mM, 75 mM, and 140 mM). HPMC viability was obtained through cell counting (WST-1).

The results are shown in FIG. 1. When HPMC was preincubated with the culture media containing no ATP, the viability of the HPMC decreased as the glucose level increased, whereas when HPMC was preincubated with the culture media containing ATP, decrease in viability caused by high level glucose was significantly alleviated.

Example 2

Instead of ATP, adenosine, which is a metabolite of ATP, was employed to study the effect of adenosine on decrease in HPMC viability caused by high level glucose.

The results are shown in FIG. 2. Adenosine exhibited no effect of alleviating decrease in HPMC viability, as shown in the case of ATP.

Example 3

Prior to the step of preincubation with ATP-containing culture media in the procedure of Example 1, HPMC were preincubated for 30 minutes with each of the following selective ATP receptor antagonists: (1) Suramin (P2X, P2Y receptor antagonist; 10 μM), (2) Reactive Blue 2 (P2Y receptor antagonist; 30 μM), and (3) PPADS (P2X receptor antagonist; 10 μM). Thereafter, the test was performed as described in Example 1.

The results are shown in FIGS. 3, 4, and 5. When the HPMC was treated with ATP receptor antagonist, ATP exhibited no effect of alleviating reduction in HPMC viability.

The results obtained in Example 1 indicate that ATP has an effect of significantly preventing peritoneal mesothelial cell injuries caused by high glucose level. The results obtained in Examples 2 and 3 reveal that this effect of ATP is not attributed to an action of ATP serving as an energy source after being taken into the cells, but rather to a direct action of ATP exhibited by the mediation of P2 receptors.

Example 4

Formulation of Peritoneal Dialysates
(1) Dialysate Containing ATP
To each of three dialysates containing glucose (1.36, 2.27, and 3.86%) are added sodium chloride, sodium lactate, calcium chloride, magnesium chloride, etc. so as to attain conventional compositional proportions, and ATP is added so that the resultant mixture attains an ATP level of 50 to 2,000 μM.
(2) Physiological Glucose Level Solution Containing ATP
To a glucose solution having physiological glucose level (0.1%) are added sodium chloride, sodium lactate, calcium chloride, magnesium chloride, etc. so as to attain conventional compositional proportions, and ATP is added so that the resultant mixture attains an ATP level of 50 to 2,000 μM.

The invention claimed is:

1. A peritoneal dialysis method comprising:
   administering into the peritoneum of a patient having uremia or renal failure a dialysate comprising adenosine triphosphate or a salt thereof; and subsequently
   discharging said dialysate from the peritoneum.

2. The peritoneal dialysis method of claim 1, wherein said patient is suffering from a renal disease, and said dialysate is administered intraperitoneally via a catheter implanted in the peritoneal cavity.

3. The peritoneal dialysis method of claim 1 or 2, wherein the concentration of adenosine triphosphate or a salt thereof in the dialysate ranges from 10 to 5,000 μM.

4. The peritoneal dialysis method of claim 1 or 2, wherein the dialysate further comprises glucose and an electrolyte.

5. The peritoneal dialysis method of claim 4, wherein the glucose level ranges from 1,000 to 4,000 mg/dL.

6. The peritoneal dialysis method of claim 1, further comprising:
   administering a dialysate containing a high level of glucose into a patient suffering a renal disease through a catheter implanted in the peritoneal cavity after administering said dialysate containing adenosine triphosphate or a salt thereof and a physiological level of glucose.

7. The peritoneal dialysis method of claim 6, wherein the physiological glucose level ranges from 0.08 to 0.16% (w/v) and the high glucose level ranges from 1,000 to 4,000 mg/dL.

8. A method for treating peritoneal injury in a subject having uremia and undergoing repeated dialysis with a peritoneal dialysate containing glucose, comprising administering an effective amount of adenosine triphosphate or a salt thereof into the peritoneum of said subject.

9. A treating method for peritoneal cell injury caused by sugar, comprising administering into the peritoneum of a subject in need thereof an effective amount of adenosine triphosphate or a salt thereof to a subject in need thereof.

10. The method as described in claim 9, wherein the cell injury caused by sugar is peritoneal mesothelial cell injury caused by glucose.

11. A peritoneal dialysis method comprising:
    administering into the peritoneal cavity of a subject having uremia an effective amount of a composition comprising adenosine triphosphate or a salt thereof; and subsequently
    discharging said dialysate from the peritoneal cavity.

12. The method of claim 11, wherein said composition further comprises glucose and electrolytes.

13. The method of claim 11, wherein said composition contains:
    10 to 5,000 μM of adenosine triphosphate or a salt thereof,
    1,000 to 4,000 mg/dL glucose,
    100 to 200 mEq/L Na$^+$,
    4 to 5 mEq/L Ca$^{2+}$,
    1 to 2 mEq/L Mg$^{2+}$, and
    80 to 120 mEq/L Cl$^-$.

14. The method of claim 13, wherein said composition also contains 30 to 50 mEq/L of an organic acid.

15. The method of claim 13, wherein said composition also contains 30 to 50 mEq/L of lactic acid.

16. The method of claim 11, wherein said composition has an osmotic pressure ranging between 300 and 700 mOsm/L.

17. The method of claim 11, wherein said subject has renal failure.

18. The method of claim 11, wherein said subject has peritoneal mesothelial cell injuries caused by exposure to high levels of sugar.

19. The method of claim 11, wherein said subject has hardening of the peritoneum or peritonitis.

20. The method of claim 11, wherein said subject has sclerotic encysted peritonitis or intractable prolonged peritonitis.

21. The method of claim 8, comprising administering a solution containing:
    adenosine triphosphate or a salt thereof,
    1,000 to 4,000 mg/dL glucose, and
    electrolytes.

22. The method of claim 9, comprising administering a solution containing:
    adenosine triphosphate or a salt thereof,
    1,000 to 4,000 mg/dL glucose, and
    electrolytes.

23. A peritoneal dialysis method comprising:
    administering into the peritoneal cavity of a patient in need of dialysis a dialysate comprising adenosine triphosphate or a salt thereof; and subsequently
    discharging said dialysate from the peritoneal cavity.

24. The peritoneal dialysis method of claim 23, further comprising a step of adding adenosine triphosphate to a conventional peritoneal dialysis solution that does not contain adenosine triphosphate to produce a dialysate and then administering said dialysate to a patient in need thereof.

25. The peritoneal dialysis method of claim 23, wherein the dialysate contains 10 to 5,000 μM of adenosine triphosphate.

26. The peritoneal dialysis method of claim 23, wherein said patient has hardening of the peritoneum or peritonitis or other damage to the peritoneum characterized by mesothelial cell injury caused by prior exposure to a peritoneal dialysis solution that does not contain adenosine triphosphate.

* * * * *